United States Patent [19]

Sawai et al.

[11] Patent Number: 5,240,700
[45] Date of Patent: Aug. 31, 1993

[54] PHARMACEUTICAL COMPOSITION COMPRISING A MEDICAMENT AND 3-OXYGERMYLPROPIONIC ACID

[75] Inventors: Kiichi Sawai; Masayasu Kurono; Kazumasa Nakano; Kyoichi Asano; Takahiko Mitani; Naohisa Ninomiya; Bunkichi Kato, all of Nagoya, Japan

[73] Assignee: Sanwa Kagaku Kenkyusho Co., Ltd., Aichi, Japan

[21] Appl. No.: 881,318

[22] Filed: May 7, 1992

Related U.S. Application Data

[63] Continuation of Ser. No. 630,634, Dec. 20, 1990, abandoned.

[30] Foreign Application Priority Data

Dec. 29, 1989 [JP] Japan .................................. 1-341810
Jul. 2, 1990 [JP] Japan .................................. 2-174961

[51] Int. Cl.$^5$ .................. A61K 31/765; A61K 33/00; A61K 9/14; A61K 9/20
[52] U.S. Cl. .................................. 424/78.37; 424/486; 424/487; 424/488; 424/451; 424/464; 424/499; 424/501; 424/436; 424/DIG. 15; 514/922
[58] Field of Search .................. 424/78, 486–487, 424/488, 451, 464, 499, 501, 78.37; 314/823

[56] References Cited

U.S. PATENT DOCUMENTS

| 4,321,273 | 3/1982 | Ishikawa et al. | 424/78 |
| 4,322,402 | 3/1982 | Ishikawa et al. | 424/78 |
| 4,889,715 | 12/1989 | Sawai et al. | 424/80 |

Primary Examiner—Thurman K. Page
Assistant Examiner—E. Webman
Attorney, Agent, or Firm—Armstrong, Westerman, Hattori, McLeland & Naughton

[57] ABSTRACT

A composition for inhibiting the degeneration of cells including liver cells by drugs and relieving the toxicity of drugs to internal organs including the liver contains as an essential component a 3-oxygermylpropionic acid polymer which is represented by:

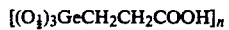

$[(O_{\frac{1}{2}})_3GeCH_2CH_2COOH]_n$ wherein n is an integer of at least 1, takes the form of a white acicular crystal and has a melting point of about 230° C. at which it decomposes or coagulates. The present composition may be used with a carrier hydroxypropylcellulose in an amount of 0.005 to 50% by weight relative to 0.005 to 5% by weight of the 3-oxygermylpropionic acid polymer.

7 Claims, No Drawings

PHARMACEUTICAL COMPOSITION COMPRISING A MEDICAMENT AND 3-OXYGERMYLPROPIONIC ACID

This application is a continuation-in-part of application Ser. No. 630,634 filed Dec. 20, 1990, abandoned.

BACKGROUND OF THE INVENTION

The present invention relates to a pharmaceutical composition for inhibiting the degeneration of cells including liver cells by drugs and relieving the toxicity of drugs to internal organs including the liver, which contains as a pharmaceutically active component an organogermanium compound with or without a suitable carrier.

The organogermanium compounds have now attracted much attention in view of their pharmacological activities. Problems with such compounds, however, are that they act differently from lot to lot and remain unclarified in terms of their specific activities (Japanese Patent Publication Nos. 46(1971)-2964 and 58(1983)-44677).

Later, it has been found that, like vinyl chloride and organosilicon compounds, the organogermanium compounds differ slightly in their polymerizability and sophisticated chemical structures and exist in the form of structures having different physical properties, resulting in the industrial preparation of their active substances being well established simultaneously with the identification of them (U.S. Pat. No. 4,309,412).

More recently, the inventors have successfully developed a process for stabilizing the high activity of the analogous compounds, whereby the reproducibility of their pharmacological activities with respect to a predetermined amount can be confirmed. This suggests that they can possibly be used in the form of various medications (U.S. Pat. No. 4,889,715).

The toxicity of drugs and poisonous substances to internal organs and their teratogenicity appear as side-effects in the case of the former and present a social problem including environmental pollution in the case of the latter. These problems can never be solved without removing their leading causes, and are thus still allowed to slumber, although the development of some antidotes is in the making.

Patients with organic diseases, esp., those with liver and kidney diseases, are so impeded in detoxication and excretion that, while having received drug treatments, they are likely to develop side effects such as disorders, e.g. anaphylaxis and acute organic malfunctions or, at worst, die of them.

Having a strong toxicity to internal organs, hard-hitting drugs for inhibiting cytotoxicity and the synthesis of nucleic acid, for instance, carcinostatics, are generally said to be a double-edged sword.

The abuses of drinking and smoking and the uptake of methyl mercury, heavy metal ions, etc. in the body cause the degeneration of tissue cells and organic disorders, becoming a social problem.

As already mentioned, it is believed that such problems can never be solved without removing their leading causes. In the case of medication, the side-effect problem may be solved to some extent by reducing dose or avoiding the use of drugs showing an increased toxicity to internal organs. For patients in need of emergent or intensive therapy, e.g. people with deadened tissue and organs, esp. those with cancer or infective diseases or pregnant women, however, it is desired to develop how to use, with greater safety, drugs showing a hard-hitting cytopathic action or a threatening toxicity to internal organs. It is also desired to establish therapy for preventing a deadening of the functioning of tissue incidental to aging.

It is therefore an object of this invention to provide a composition for inhibiting the degeneration of cells including liver cells by drugs and relieving the toxicity of drugs to internal organs including the liver, which meets such demands.

SUMMARY OF THE INVENTION

According to this invention, the above-mentioned object is achieved by the provision of a composition for inhibiting the degeneration of cells including liver cells by drugs and relieving the toxicity of drugs to internal organs including the liver, which contains as an essential component a 3-oxygermylpropionic acid polymer which is represented by:

$$[(O_{\frac{1}{2}})_3GeCH_2CH_2COOH]_n$$

wherein n is an integer of at least 1, takes the form of a white acicular crystal and has a specific gravity (density) of 2.23, a solubility of 1.57 in water at 20° C. and a melting point of about 230° C. (at which it decomposes or coagulates). The composition of this invention may contain a carrier for activating the essential component such as hydroxypropylcellulose, and may be used in combination with a substance showing an increased cytopathogenicity and/or a substance showing a threatening toxicity to internal organs. That carrier may be used in an amount of 0.005 to 50% by weight relative to 0.05 to 5% by weight of the essential component.

The compositions according to this invention can be administrated, with greater safety, to patients with a deadening of the functioning of organs including the liver and the kidney, brain tissue and cells or pregnant women or infants with an increased proliferation of cells, when they develop cancer, infective diseases or other afflictions and receive drug treatments, thereby relieving or eliminating their side effects.

The compositions according to this invention can also be used to repair the functioning of cells damaged or deadened by contact with substances showin a strong degenerative action to tissue and a threatening toxicity to internal organs. Moreover, the compositions according to this invention may be administrated to those who are engaged in the synthesis of organic materials and so frequently have chances of handling toxic reagents and chemicals, addicts such as habitual smokers and drinkers or patients with chronic disease-inducing viruses, thereby preventing the development of organic diseases or their conditions from becoming more serious.

DETAILED DESCRIPTION OF THE INVENTION

Substances having a threatening toxicity to internal organs, with which the compositions of this invention are advantageously used, include lenitives based on propionic acid such as indomethacin; antibiotics based on kanamycin; toxic substances based on mercury; alcohol; substances based on carbon tetrachloride; brain-barrier penetrating carcinostatics having a threatening toxicity to the brain; cytotoxic substances; poisonous gases based on carbon oxides; and the like. The present invention is also advantageously used with substances having an increased cytopathogenicity such as mercuric chloride and teratogens.

For preparing the composition of this invention, a pharmaceutical carrier may be used to make the effective component soluble or pharmacologically stable.

The composition of this invention may be used alone or in combination with drugs showing an increased toxicity to internal organs and causing a considerable tissular degeneration such as (1) antibiotics (based on penicillin, cephalosporin, kanamycin, tetracycline and streptomycin, (2) antiphlogistics and lenitives (indomethacin), (3) carcinostatics and virucides (mitomycin, tegafur, 5-fluorounecil (5-Fu, cisplatin and other drugs for inhibiting cytotoxicity and the synthesis of nucleic acid) and (4) addictive nacrotics, hypnotics and tranquilizers. To this end, carriers such as lactose and albumin are preferably used to maintain the activity of the effective component. The compositions of this invention may be per so administrated to patients in the form of e.g. tablets and capsules.

Although varying depending upon the type of the essential component, the type of the composition, the age of patients, etc., the composition of this invention may be per os administrated to humans at a dose in the range of generally 10 to 1500 mg/kg and to adults (weighing 50 kg) at a dose of 150 mg/day.

EXAMPLES

The present invention will not be explained in greater detail with reference to the following examples. Preparation Example 1-Preparation of Activated Composition Using ethanol as a wetting agent, hydroxypropylcellulose was kneaded with 3-oxygermylpropionic acid at 2:1, and was then dried at a temperature lower than 50° C. to obtain a powdery or granular composition.

PREPARATION EXAMPLE 2

Tablet

The composition of Preparation Example 1 was blended with the following vehicle and other components, and the blend was then tableted in a conventional manner.

| Component | Amount (mg) |
| --- | --- |
| Composition of Preparation Ex. 1 | 100 |
| Lactose | a proper quantity |
| Carboxymethylcellulose (Ca) | 7 |
| Crystalline cellulose | 40 |
| Magnesium stearate | 7 |
| | 200 mg per tablet |

PREPARATION EXAMPLE 3

Tablet

The composition of Preparation Example 1 was blended with the following vehicle and other components, and the blend was then tableted in a conventional manner.

| Component | Amount (mg) |
| --- | --- |
| Composition of Preparation Ex. 1 | 100 |
| Lactose | a proper quantity |
| Methylcellulose | 20 |
| Hydroxypropylcellulose | 8 |
| Sucrose fatty acid ester | 2 |
| Magnesium stearate | 2 |

| Component | Amount (mg) |
| --- | --- |
| Sodium lauryl sulfate | 1 |
| | 200 mg per tablet |

PREPARATION EXAMPLE 4

Tablet

| Component | Amount (mg) |
| --- | --- |
| Composition of Preparation Ex. 1 | 100 |
| Indomethacin | 20 |
| Lactose | a proper quantity |
| Methylcellulose | 20 |
| Hyroxypropylcellulose | 8 |
| Sucrose fatty acid ester | 2 |
| Magnesium stearate | 2 |
| Sodium lauryl sulfate | 1 |
| | 200 mg per tablet |

PREPARATION EXAMPLE 5

Capsule

A blend of the composition of Preparation Ex. 1 with the following vehicles was encapsulated in a conventional manner.

| Component | Amount (mg) |
| --- | --- |
| Composition of Preparation Ex. 1 | 100 |
| Indomethacin | 20 |
| Lactose | 40 |
| Corn starch | 38 |
| Magnesium stearate | 2 |

PREPARATION EXAMPLE 6

Suppository

The composition of Preparation Ex. 1 was dispersed in a higher fatty acid glyceride, and the dispersion was then formed into a suppository in a conventional manner.

| Component | Amount (mg) |
| --- | --- |
| Composition of Preparation Ex. 1 | 60 |
| (3-oxygermylpropionic acid) | (20) |
| 5-fluorouracil | 100 |
| Cacao butter | 1540 |
| | 1700 mg per suppository |

PHARMACOLOGICAL TEST EXAMPLE I

I-A. Toxicity Reagent

With (a) the 3-oxygermylpropionic acid according to this invention (hereinafter called SK-818) and (b) the composition of Preparation Ex. 1, SD rats and mice were subjected to acute and subacute (chronic) toxicity tests in a conventional manner. The results are reported below. (Groups of animals, 8–10 per group, were used for experimentation.)

i. Acute Toxicity

| LD50 (mg/kg) | per os (no significant difference between (a) and (b)) |
| --- | --- |

-continued

| | | |
|---|---|---|
| Mice, | male | 5,600 or more |
| | female | 5,800 or more |
| Rats, | male | 7,700 or more |
| | female | 7,050 or more |

Between (a) SK-818 and (b) the composition of Preparation Ex. 1 there was no significant difference in acute toxicity. While the test group to which SK-818 was administrated developed general symptoms of calming-down, diarrhoea, vomiting and typhlectasis, the test group to which the composition of Preparation Ex. 1 did not substantially show any special symptoms.

ii. Subacute Toxicity (a) SK-818 and (b) the composition of Preparation Ex. 1 were per os administrated to SD masculine rats at doses of 256, 380, 640, 1300, 1600 and 4000 mg/kg/day over three months to determine their doses at which they had no toxic influence on the animals and the animals were absolutely poisoned, respectively.

The dose of SK-818 which had no toxic influence on the animals was 256 mg/kg, and the dose of SK-818 at which the animals were absolutely poisoned was 1600 mg/kg. At 4000 mg/kg, some animals died. After the lapse of five weeks, however, the survivors recovered from poisoning.

The dose of the composition of Preparation Ex. 1 which had no toxic influence on the animals was 380 mg/kg, and its dose causing the animals to be absolutely poisoned was 1300 mg/kg. All the animals were left alive. I-B. Effects on inhibiting the heteroplasia of liver cells and relieving hepatoxicity in liverish models Effect on relieving hepatoxicity in rats with hypohepatia Because the composition of Preparation Ex. 1 was found to be more efficacious than SK-818 in the subacute toxicity test, the following experimentation was carried out with this composition.

Carbon tetrachloride was per os administrated as a hepatoxic substance to SD masculine rats (weighing 500 g ± 50 g; age, 10 months) with hypohepatia (3 groups containing 8-9 rats each) at a dose of 0.5 g/kg, whereby their serum GOT was increased to more than 50 Karmen units after 24 hours. At the same time, 2 mg/kg of indomethacin as a hepatoxic drug (a lenitive), 5 mg/kg of 5-FU as a hepatoxic carcinostatic and 10 mg/kg of tetracycline as a hepatoxic antibiotic were per os administrated to each of the animals five times every fourth day.

An additional 20 mg/kg of the composition of Preparation Ex. 1 was per os administrated to the medicated group.

Seven days after the completion of medication, the animals were slaughtered to remove the livers, which were then visually observed. Afterwards, the tissue slices were observed under an optical microscope to examine the degree of heteroplasia of the liver cells.

The GOT eluates due to cytoclasis were determined by gathering blood from the tail vein of each animal 24 hours after the administration of carbon tetrachloride, two and ten days after the initiation of medication and on the final date of experimentation.

From the results reported in Table 1, it was found that, in the test groups, blood-GOT levels begun increasing just after the administration of the hepatoxic substances and reached more than 80 Karmen units signifying the aggravation of hepatopathy while, in the groups treated with the composition of Preparation Ex. 1, there was a significant drop of blood-GOT levels.

Referring to the degree of heteroplasis of liver cells examined by autopsy, the assay of tissue indicated that even in the control group, there is swelling due to the aged animals and a decrease in the number of basophiles over the lobule. In the groups to which only the hepatoxic substances were administrated, a number of fibrogeneses were found and a part of the liver tissue contained a cellular colony containing such cells as large polynuclear cells. Even in the groups to which indomethacin and 5-FU were administrated, some animals died. In the test groups which were further treated with the composition of Preparation Ex. 1, all the animals were left alive. The results of autopsy indicated that there is swelling and some tissue necroses, but the assay of tissue showed that there is no heteroplasis of liver cells.

TABLE 1

Changes in serum GOT in Karmen units/ml
51.3 ± 2.31 as measured 24 hours after the administration of carbon tetrachloride

| | 2 days after the initiation of medication | 10 days | Final Date |
|---|---|---|---|
| Control group | 64.0 ± 5.47 | 25.6 ± 3.54 | 23.8 ± 1.96 |
| Test groups | | | |
| (i) | 81.3 ± 4.21 | 91.8 ± 8.35 | 99.4 ± 1.43 |
| (ii) | 78.5 ± 2.31 | 83.8 ± 2.41 | 96.1 ± 3.24 |
| (iii) | 83.2 ± 6.35 | 82.0 ± 5.97 | 89.6 ± 2.51 |
| Test groups treated with the composition of Preparation Ex. 1 | | | |
| (i) | 71.3 ± 2.31 | 46.4 ± 1.35 | 15.3 ± 2.53 |
| (ii) | 73.6 ± 6.35 | 43.2 ± 3.54 | 19.3 ± 3.18 |
| (iii) | 80.1 ± 3.72 | 56.1 ± 2.71 | 12.0 ± 8.31 |

(i): Indomethacin
(ii): 5-FU
(III): Tetracycline

I-C. Effect on inhibiting the action of a hepatocyte-damaging substance on cultivated liver cells An effect on relieving the culture damage induced by adding hepatocyte-damaging substances and SK-818 to hepatocyte culture systems was examined by measuring the activity of glutamic-pyruvic transaminase (GPT) eluates obtained by cellular disorders. How much the elution of GPT was inhibited was used as an index to the hepatoxicity-relieving effect.

The following four substances were used as the hepatocyte-damaging (hepatoxic) substances.
(a) Galactosamine - "J. Natur. Prod.", 46, 841, 1983.
(b) Calcium ionophore - "Pharmacognosy", 39, 218, 1985.
(c) Cumene hydroperoxide - "Planta Med.", 51, 50, 1985.
(d) 1-Napthylisothiocyanate.

The extraction and culture of a single layer of rat's hepatocytes were carried out by the procedures described by Nakamura et al in "Protein, Nucleic Acid and Oxygen", Extra Number No. 24, pp. 55-74, 1981.

Single layers of rat's heptaocytes were cultured for certain periods of time—0 hour for a galactosamine group, 20.5 hours for calcium ionophore and cumene hydroperoxide groups, and 14.5 hours for a 1-napthylisocyanate group. Afterwards, the hepatocyte-damaging substances were added to the culture media at the respective desired concentrations - 0.35 mM for (a); 10 μm for (b), 0.5 mM for (c) and 188 μm for (d)), which were then cultured for the respective given periods of time - 38 hours for the group (a), 1 hour for (b), 1 hour for (c) and 12 hours for (d).

SK-818 was dissolved in bovine embryo serum, and the serum solution was then added to each medium at the respective stages of culture in the following three manners;

(a) it was added to the pre-culture medium prior to the addition of the hepatocyte-damaging substance (called the pre-addition);

(b) it was added to the culture medium simultaneously with the addition of the hepatocyte-damaging substance (called the simultaneous addition); and (c) it was added to the pre-culture and culture media (called the total addition).

The activity of the GPT eluates produced by cytotoxicity in the media was measured by a GPT measuring kit. Then, GPT reductions in % were found by the following equation:

$$GPT \text{ reductions } (\%) = \frac{(B - A) - (C - A)}{(B - A)} \times 100$$

wherein
A is the activity in Karmen units of GPT in a culture medium to which no hepatocyte-damaging substance is added,
B is the activity in Karmen units of GPT in a culture medium to which the hepatocyte-damaging substance is added, and
C is the activity in Karmen units of GPT in a culture medium to which the hepatocyte-damaging substance is added together with 3-oxygermyl-propionic acid.

Results

The following GPT reductions were obtained.

(a) Addition of galactosamine

29% in the case of the simultaneous addition of SK-818.

(b) Addition of calcium ionophore

27% in the case of the simultaneous addition
27% in the case of the simultaneous addition of SK-818, and
36% in the case of the total addition of SK-818.

(c) Addition of cumene hydroperoxide

63% in the case of the simultaneous addition of SK-818, and
42% in the case of the total addition of SK-818.

(d) Addition of 1-naphtylisothiocynatate

79% in the case of the simultaneous addition of SK-818, and
67% in the case of the total addition of SK-818.

No GPT reduction was achieved only by the pre-addition of SK-818. In other words, it was only when SK-818 was used in combination with the hepatocyte-damaging substances that significant GPT reductions were obtained. This implies that SK-818 has an extracellular inhibiting effect.

I-D. Clinical test of SK-818 for Type B chronic hepatitis (a) Object

The efficacy of SK-818 against Type B chronic hepatitis was examined, using a placebo as control.

(b) Subject

The subjects were patients who has been diagnosed by biopsy as chronic hepatitis before at most one year in principle, were positive to HBe antigens and had Type B chronic hepatitis in need of treatment.

(c) Drug under test and control (i) The drug under test was a capsule containing 10 mg of SK-818.
(ii) The control consisted only of lactose (a placebo).

(d) Administration

The subjects followed the standard prescription of three capsules a day and one capsule each meal over 16 weeks in principle.

(e) What was measured:

The general examination of the functioning of the livers and blood and the measurement of HBe antigens and antibodies were all carried out by the Virus Hepatitis Research Foundation.

(f) Participants

TABLE 2

| | | Number of cases | | |
|---|---|---|---|---|
| | | SK-818 | Placebo | Total |
| Sex | male | 81 | 63 | 144 |
| | female | 20 | 18 | 38 |
| Age | ~19 | 2 | 1 | 3 |
| | 20~29 | 31 | 23 | 54 |
| | 30~39 | 39 | 27 | 66 |
| | 40~49 | 18 | 21 | 39 |
| | 50~59 | 9 | 5 | 14 |
| | 60~ | 2 | 4 | 6 |
| | Average | 35.2 | 37.1 | 36.0 |
| Duration | CAH | 78 | 63 | 141 |
| | CIH | 17 | 13 | 30 |
| Day-patients | Day-patients | 83 | 73 | 156 |
| In-patients | In-patients | 4 | 1 | 5 |
| | Day-and In-patients | 14 | 7 | 21 |
| Complications | not developed | 89 | 72 | 161 |
| | developed | 12 | 9 | 21 |

(g) Results

Diagnoses of the physicians in charge as to how the functioning of the livers was ameliorated are reported in Table 3 and the statistics in Table 4.

As will be seen from the rate of amelioration of "slightly ameliorated—57. 9%" or more reported in Table 4, most of the patients show a reduced or limited elution of enzymes in liver cells. This suggests that the activity of Type B hepatitis-associated viruses is inhibited by SK-818.

TABLE 3

| ESTimation Drugs | Degree of Amelioration (determined by physicians) | | | | | | | | Rate of Amelioration | |
|---|---|---|---|---|---|---|---|---|---|---|
| | Remarkably ameliorated | Ameliorated to some extent | Slightly ameliorated | Nochange | Less aggravated | aggravated | seriously aggravated | Total | Ameliorated to some or higher extent | Slightly ameliorated or more |
| SK-818 | 12 | 23 | 20 | 31 | 5 | 4 | 0 | 95 | 36.8 | 57.9 |
| Placebo | 6 | 6 | 9 | 22 | 16 | 8 | 1 | 68 | 17.6 | 30.9 |
| Total | 18 | 29 | 29 | 53 | 21 | 12 | 1 | 163 | | |
| Mann-Whitney's U Assay | | | | $Z_0 = 3.997$ $P = 0.0001^{***}$ | | | | Fisher's direct calculation | $P = 0.0114^*$ | $P = 0011^{**}$ |

$^*P < 0.05$ $^{}P < 0.01$ $^{*}P < 0.001$
[P: accuracy (probability)]

TABLE 4

| | SK-818 | | | | | | Statistics Placebo | | | | | | Differences between groups | |
|---|---|---|---|---|---|---|---|---|---|---|---|---|---|---|
| | 4 W | 8 W | 12 W | 16 W | Af4 W | Af8 W | 4 W | 8W | 12 W | 16 W | Af4 W | Af8 W | | |
| HBe antigens (EIA) log | ↓*** | ↓** | ↓*** | ↓*** | ↓*** | ↓*** | | | | | | ↓* | 4 W** | 12 W* |
| | | | | | | | | | | | | | 16 W* | Af4 w* |
| HBe antibodies (RIA %) | ↑* | ↑* | ↑** | ↑* | ↑* | ↑** | | | | | | | 4 W* | 12 W* |
| | | | | | | | | | | | | | 16 W* | Af8 w+ |
| GOT | ↓* | ↓+ | ↓*** | ↓*** | ↓** | ↓** | | | | | | | 12 W* | |
| | | | | | | | | | | | | | 16 W+ | |
| GPT | ↓* | ↓** | ↓*** | ↓*** | ↓** | ↓** | | | | | | | 8 w* | 12 w** |
| | | | | | | | | | | | | | 16 W* | Af4 w* |
| LDH (mu/ml) | ↓+ | ↓+ | ↓* | | | | | | | | | | | |
| AIP (KA) | | ↓+ | ↓+ | | | | | | | | | | | |
| γ-GTP (mu/ml) | | ↓** | ↓** | ↓** | ↓* | | | | | | | | 16 w+ | |
| Total Bilirubin (mg/dl) | ↓* | | | | | | | | | | | | 4 w+ | |
| | | | | | | | | | | | | | 8 W* | |
| Direct Bilirubin (mg/dl) | | | | | | | | ↑** | | | | | 4 w+ | |
| | | | | | | | | | | | | | 8 W* | |
| Cholinesterase (ΔPH) | | ↑* | ↑* | | ↑* | ↑** | ↓* | ↓+ | ↓* | | | | 4 w* 8 w** | 12 W** Af4 W* 16 w* Af8 w+ |
| Total serum Protein (g/dl) | | | | | | | | | | | | | | |
| Total Cholesterol (mg/dl) | | ↑* | ↑* | ↑* | | ↑* | | | | | | | 8 W* 12 W** | 16 W** Af8 w* |
| Serum Albumin (g/dl) | | ↑* | ↑+ | | | | | | | | | | | |
| TTT | | | ↓** | ↓*** | ↓*** | ↓* | | | ↓* | ↓+ | | | Af4 w+ | |
| ZTT | | ↓** | ↓** | ↓** | ↓* | | ↓+ | ↓* | ↓* | | | | | |
| γ-Globulin (g/dl) | | ↓** | ↓*** | ↓*** | ↓* | | | | | | | | 12 W+ 16 w+ | Af4 w* Af8 w+ |

$^{*} P = 0.001$ $^{}P < 0.01$ $^*P < 0.05$ $\ddagger: P < 0.10$
W: Weeks Af4 W: after 4 weeks Af8 W: after 8 weeks ↓: drop(decrease) ↑: rise (increase)

PHARMACOLOGICAL TEST EXAMPLE II

II-A. Action of SK-818 on preventing nephritis (a) Object

The action of SK-818 on preventing the development of spontaneous nephritis of MRL/1 mice (or a deadening of the functioning of the kidney associated with aging) was examined.

(b) Procedures

Given amounts (0.1 mg/kg, 1.0 mg/kg and 10.0 mg/kg a day) of SK-818, in the form of a mixture of the composition of Preparation Ex. 1 with feed, were per os administrated to MRL/1 masculine mice of six-week age (16 for each group) twice a week over 12 weeks. In the meantime, urinary protein was measured once a week; urinary protein levels exceeding 100 mg/dl were taken as positive. Examination was then made of how many animals became positive at the respective week-ages. Moreover, blood-urinary nitrogen levels were determined on the day following the final administration to make serological/physiological and pathological estimations of the action of SK-818 on nephritis.

The urinary protein and blood-urinary nitrogen levels were measured with Protein Pre-test (made by Wako Junyaku K. K.) and Urinary Nitrogen B-Test according to the urease/indophenol method (made by Wako Junyaku K. K.), respectively.

(C) Results

The results are reported in Tables 5 and 6.

As can be seen from the data, the control group shows an increase in the urinary protein levels from 15 or 16 weekage, but the test groups do not. At 10 mg/kg, the increase in the urinary protein levels is remarkably inhibited (see Table 5).

This also holds for the blood-urinary nitrogen levels. At 10 mg/kg, the increase in the blood-urinary nitrogen levels is significantly inhibited (see Table 6).

In general, MRL/1 mice develop major symptoms of membranoproliferative glomerulonephritis. In the control group, 57% of glomeruli becomes more morbid, but only 23–34% does in the groups medicated with SK-818. Thus, it is found that SK-818 produces an inhibitory action on the spontaneous development of nephritis in MRL/1 mice.

Altogether, SK-818 is efficacious against the development of spontaneous nephritis in MRL/1 mice from the standpoints of serology/physiology and pathology.

TABLE 5

| Number of animals with positive urinary protein levels | | | |
|---|---|---|---|
| Amount of SK-818 | 16 week-age | 17 week-age | 18 week-age |
| Control | 7/15 | 9/15 | 13/15 |
| 0.1 m/kg | 4/15 | 7/15 | 10/15 |
| 1 mg/kg | 4/15 | 6/15 | 8/15 |
| 10 mg/kg | 2/15 | 4/15 | 8/15 |

In Table 5, 7/15, for instance, means that 7 in 15 became positive.

TABLE 6

| Blood-urinary nitrogen levels | |
|---|---|
| Amount of SK-818 | BUN (mg/kg) |
| Control | 39.5 ± 3.9 |
| 0.1 mg/kg | 32.2 ± 1.6 |
| 1 mg/kg | 35.5 ± 3.3 |
| 10 mg/kg | 29.3 ± 1.7 |

II-B. Action of SK-818 on relieving the nephrotoxicity of mercuric chloride (a) Object An effect of SK-818 on a deadening of the functioning of the kidney by mercuric chloride was examined, using blood-urinary nitrogen levels as an index.

(b) Procedures

Mercuric chloride was subcutaneously administered to Wistar masculine rats of seven-week age, 6–10 per group, at a dose of 1.2 mg/kg. From 24 hours after the administration till the lapse of 96 hours, the animals were permitted to freely drink an aqueous solution containing 2,400 ppm of SK-818 (at an average dose of 231±14 mg/kg). Blood was gathered before and just after the administration of mercuric chloride as well as the lapse of 24, 48, 72 and 96 hours to measure blood-urinary nitrogen levels.

(c) Results

The results are reported in Table 7.

The groups all showed a maximum blood-urinary nitrogen level after 48 hours. In the group medicated with SK-818, however, the blood-urinary nitrogen levels decreased sharply from the peak value, as time went by. This suggests that SK-818 is efficacious against a deadening of the functioning of the kidney by the administration of mercuric chloride.

TABLE 7

(Effect of SK-818 on blood-urinary nitrogen levels after administration of mercuric chloride)

| Groups | Blood-urinary nitrogen (mg/dl) | | | | |
|---|---|---|---|---|---|
| | 0 hour | 24 hours | 48 hours | 72 hours | 92 hours |
| Untreated (n = 6) | 19.1 ± 0.3 | — | 15.8 ± 0.6 | — | 14.1 ± 0.5 |
| Control (n = 10) | 18.0 ± 0.4 | 36.1 ± 1.9 | 69.5 ± 11.1 | 64.8 ± 19.6 | 43.0 ± 17.4 |
| SK-818 (2400 ppm aqueous solution) | 15.1 ± 0.4 | 31.9 ± 1.3 | 50.6 ± 9.8 | 45.9 ± 13.8 | 30.9 ± 9.4 |

II-C. Effect of SK-818 on amnesia induced by carbon dioxide (a) Procedures

A ddy masculine mice was encaged in a bright chamber of a testing box (comprising bright and dark chambers, each measuring 15.0×17.5×18.5 cm and provided with an inlet/outlet combination of 6.0×6.0 cm), and the time which it took the animal to walk into the dark chamber (the reaction potential time during acquisition, hereinafter referred to as A.T.) was then measured. From just after the animal walked into the dark chamber, foot shocks of 2.5 mA were continuously applied to the animal through a floor's grid with a shock generator scrambler, made by Astech Co., Ltd., until the animal walked into the bright chamber. Immediately after the acquisition trial, the animal was encaged in a desiccator, and 15 l/min of $CO_2$ gas were injected into the desiccator for 40 to 45 seconds for suffocation. After the animal was removed from the desiccator, artificial aspiration was immediately tried thereon. The animal was then put back in a home case.

After 24 hours of the acquisition trial, the animal was again encaged in the bright chamber of the testing box to measure the time which it took the animal to walk into the dark chamber (or the reaction potential time during the retention trial, hereinafter referred to as R.T.). SK-818, in the form of a mixture with feed, had been per os administrated to the animal from 3 days before at a dose of 10.0 mg/kg/day. (b) Results The results of dysmnesia models induced by the loading of $CO_2$ gas are reported in Table 8, from which it is found that SK-818 gives rise to a significant increase in R.T., and so is efficacious against dysmnesia.

TABLE 8

| | Number of animals | A.T. In sec. | R.T. in sec. |
|---|---|---|---|
| Group A | | 51.8 ± 9.1 | 189.4 ± 19.2 |
| B | 26 | 48.5 ± 9.1 | 276.5 ± 19.3 |
| C | 15 | 50.7 ± 19.7 | 360.0 or longer |

TABLE 8-continued

| | Number of animals | A.T. In sec. | R.T. in sec. |
|---|---|---|---|
| C | 15 | 51.3 ± 5.2 | 68.3 ± 11.1 |

Group A: Foot Shocks + CO$_2$ Gas
B: SK-818 + Foot Shocks + CO$_2$ Gas
C: Foot Shocks
D: CO$_2$ Gas

What is claimed is

1. An orally administerable composition for ameliorating toxic side effects of a drug in a human which comprises the drug in combination with a toxic side effect ameliorating amount of a 3-oxygermylpropionic acid polymer of the formula:

$$[(O_{\frac{1}{2}})_3GeCH_2CH_2COOH]_n$$

wherein n is an integer of at least 2 and the acid is in the form of white acicular crystals melting at about 230° C.

2. The composition of claim 1, wherein the drug is a lenitive, an antibiotic or a brain-barrier penetrating carcinostatic.

3. The composition of claim 1, wherein the drug is cytotoxic.

4. The composition of claim 1, wherein the drug is hepatoxic.

5. The composition of claim 1, wherein the drug is indomethacin, streptomycin, kanamycin, cephalosporin, penicillin, mitomycin, 5-fluorouracil, cisplatin or derivatives thereof.

6. The composition of claim 1, further comprising a carrier.

7. The composition of claim 6, wherein the carrier is hydroxypropylcellulose.

* * * * *